(12) United States Patent
Srinivasan et al.

(10) Patent No.: US 8,633,354 B2
(45) Date of Patent: Jan. 21, 2014

(54) DEVELOPMENT OF VERY EARLY FLOWERING AND NORMAL FRUITING PLUM WITH FERTILE SEEDS

(75) Inventors: Chinnathambi Srinivasan, Martinsburg, WV (US); Ralph Scorza, Shepherdstown, WV (US); Ann Callahan, Shepherdstown, WV (US); Chris Dardick, Shenandoah Junction, WV (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 442 days.

(21) Appl. No.: 12/761,190

(22) Filed: Apr. 15, 2010

(65) Prior Publication Data
US 2011/0067147 A1 Mar. 17, 2011

Related U.S. Application Data

(60) Provisional application No. 61/212,708, filed on Apr. 16, 2009.

(51) Int. Cl.
*A01H 5/00* (2006.01)
*A01H 5/10* (2006.01)
*A01H 1/00* (2006.01)
*C12N 15/82* (2006.01)

(52) U.S. Cl.
USPC .................. 800/278; 800/290; 800/298

(58) Field of Classification Search
None
See application file for complete search history.

(56) References Cited

U.S. PATENT DOCUMENTS

2008/0066198 A1 * 3/2008 Nilsson et al. ............... 800/265

* cited by examiner

*Primary Examiner* — Stuart F Baum
(74) *Attorney, Agent, or Firm* — John D. Fado; Evelyn M. Rabin

(57) ABSTRACT

To produce early flowering genotypes, plum (*Prunus domestica*) was transformed with the poplar (*Populus trichocarpa*) Flowering Locus T1 (PtFT1) gene. Ectopic expression of 35S::PtFT1 Induced early flowering in vitro from transgenic plantlets within two months of transformation. When the transgenic plum plants were rooted and transferred to soil and grown in posts in the growth chamber, a number of additional lines flowered. Normal flowering and fruiting were observed in the greenhouse within one year of transformation. While dormancy was not necessary for growth or fruiting, FT plums were still winter hardy and floral bud set and flowering responded normally to changes in temperature. By manipulating a single gene, temperate tree crops can be effectively engineered for cultivation in new growing areas and for entirely new modes of agricultural production that are continuous, sustainable, and adaptable to climate change.

23 Claims, 12 Drawing Sheets
(10 of 12 Drawing Sheet(s) Filed in Color)

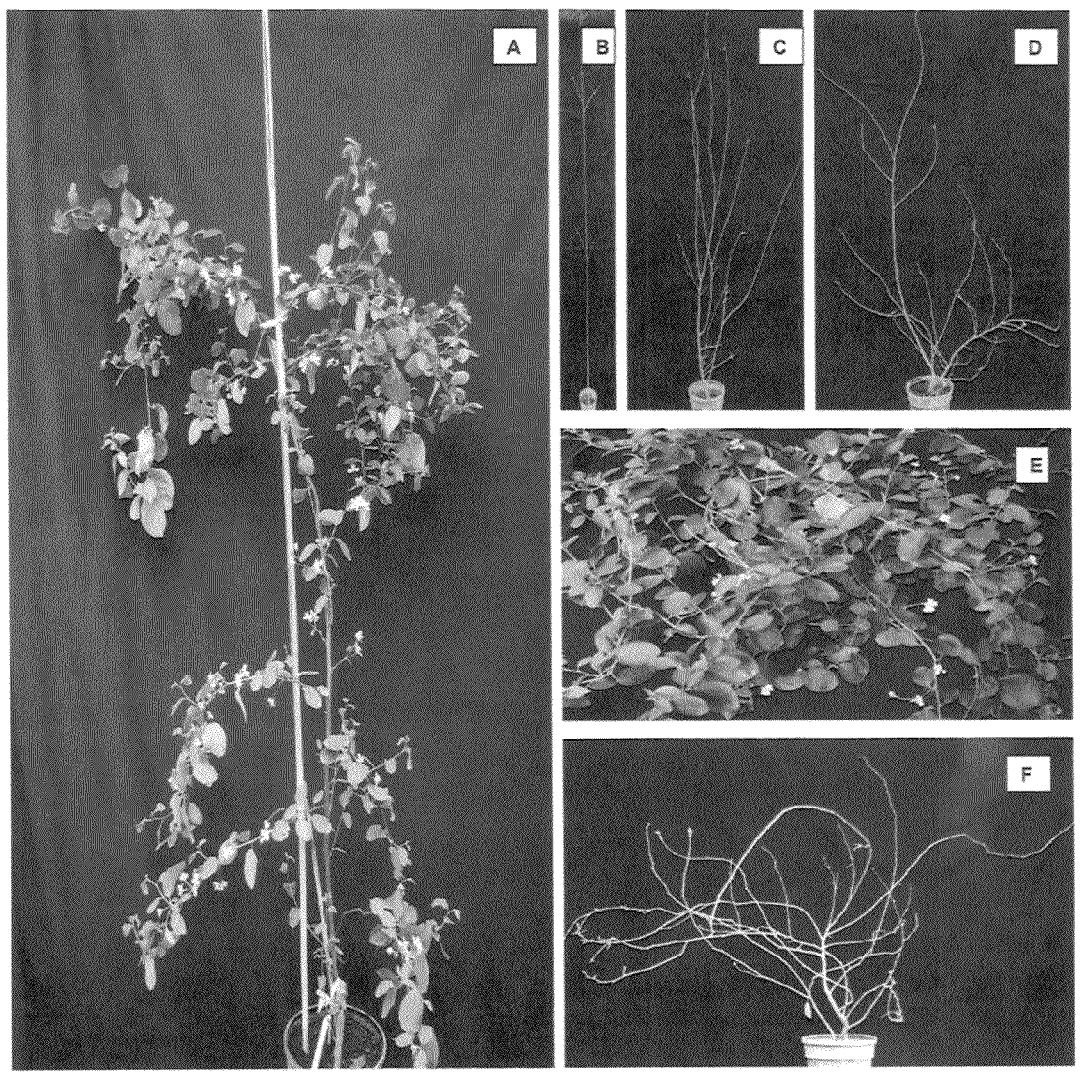
Fig. 1A-F

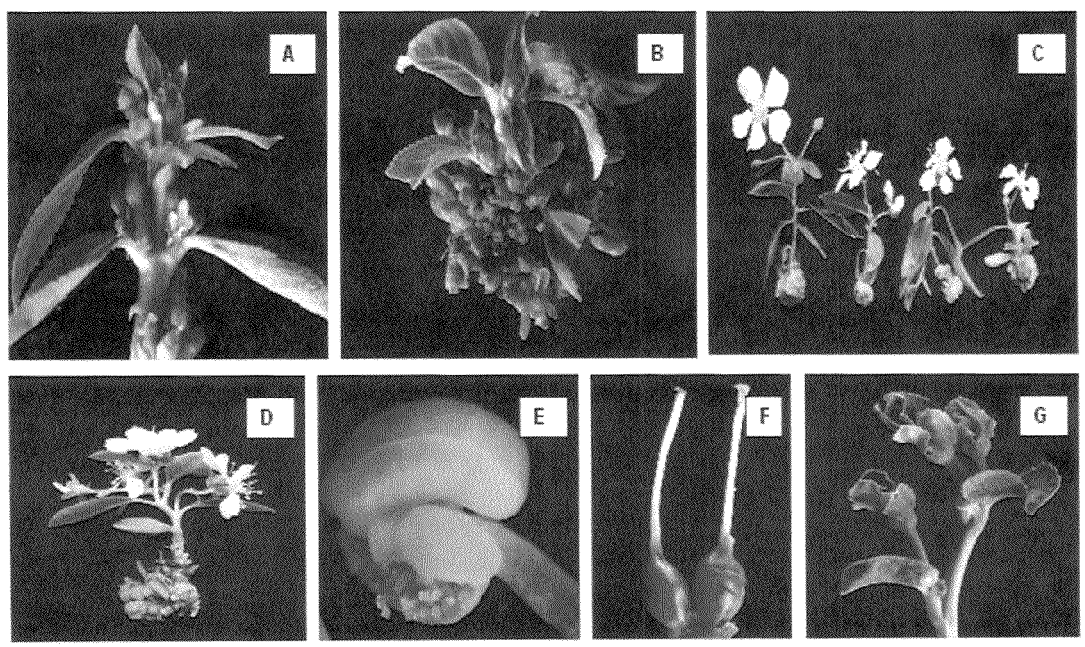
Fig. 2A-G

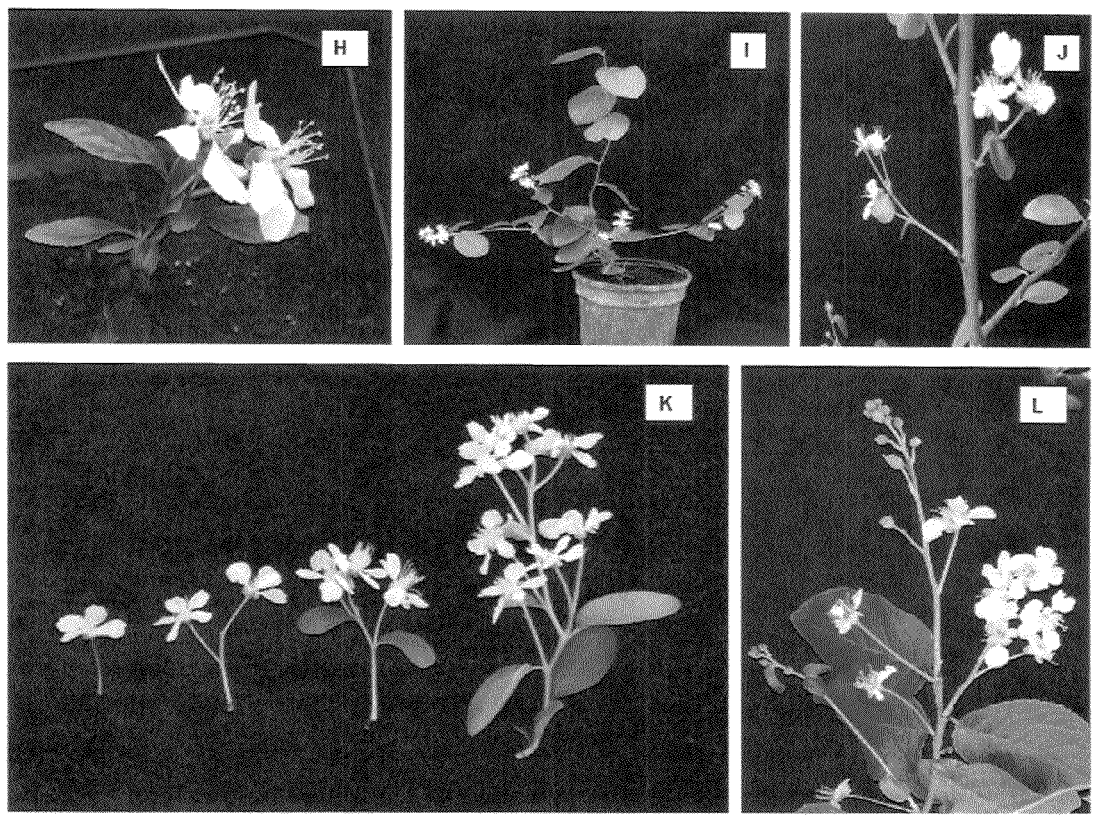
Fig. 2H-L

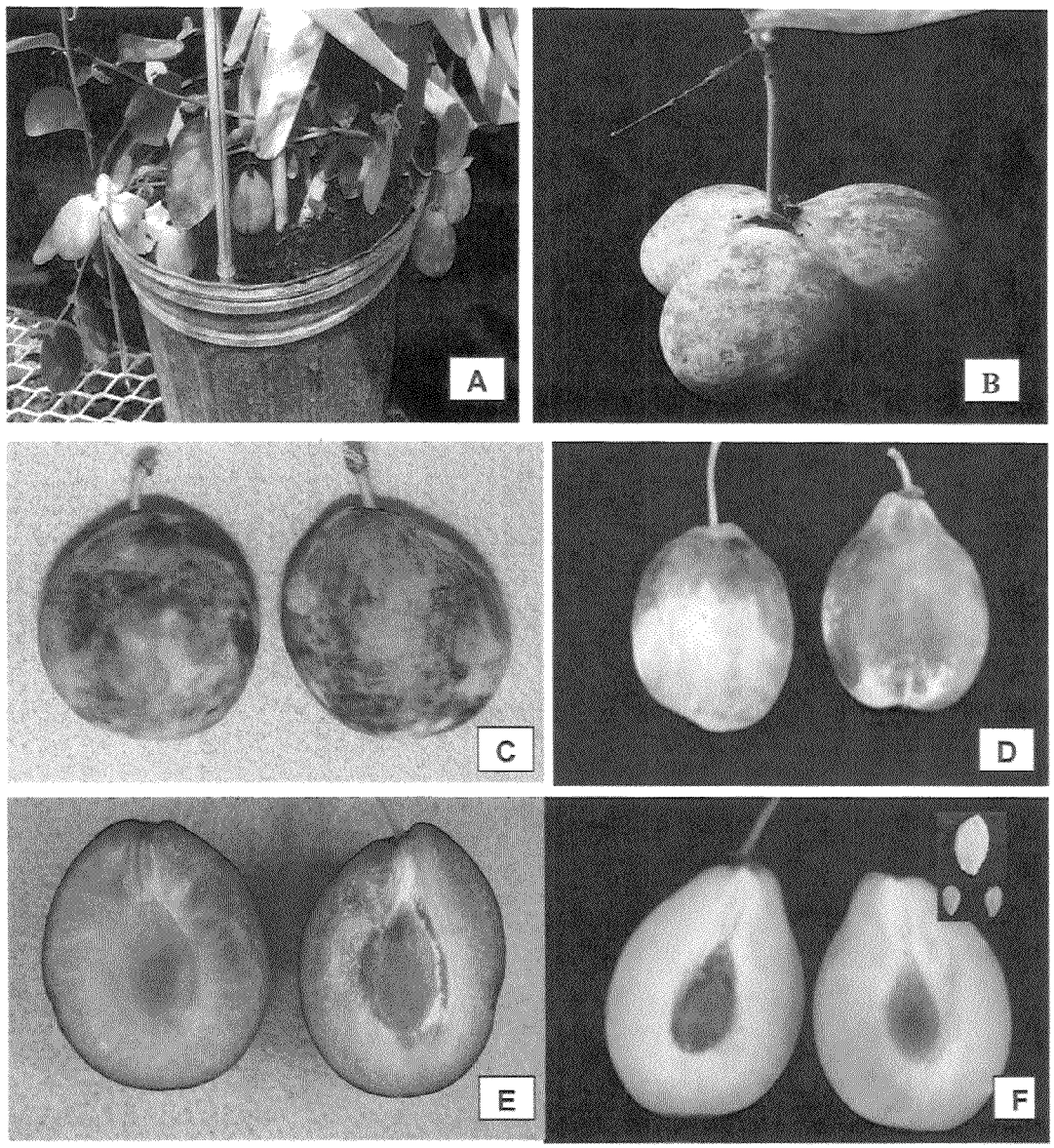
Fig. 3A-F

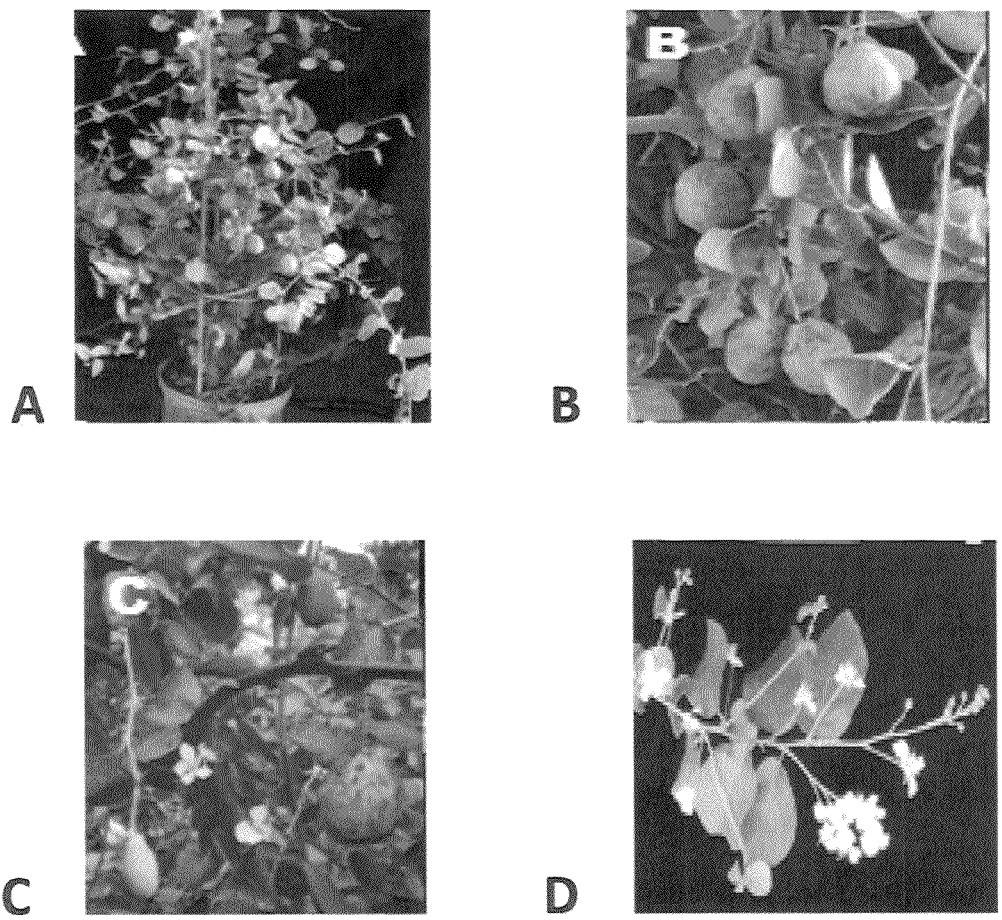
Fig. 4A-D

Fig. 6A-B
Fig. 7

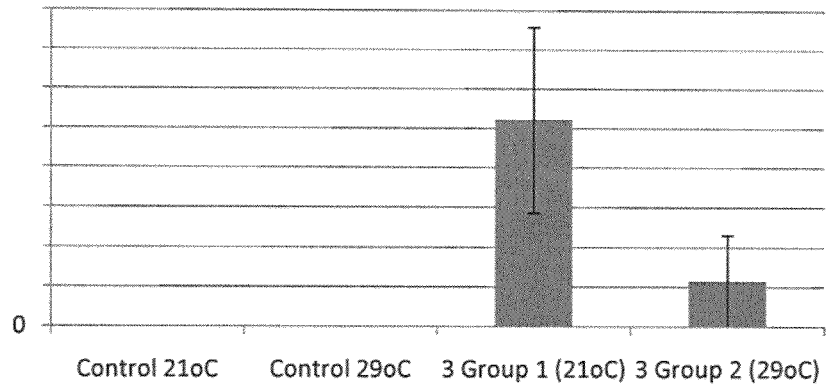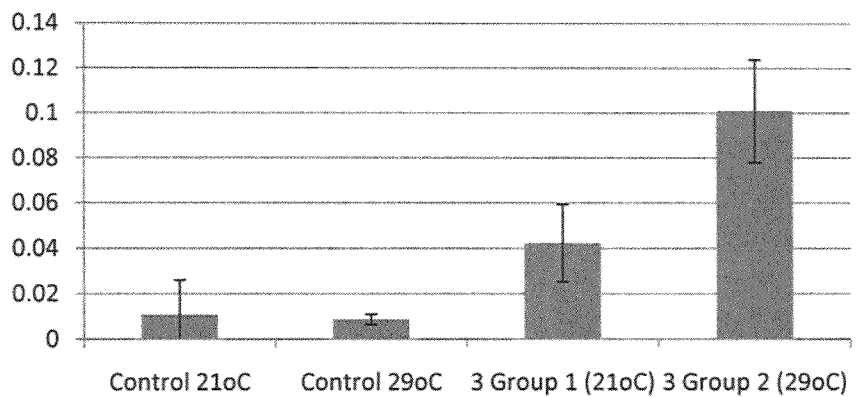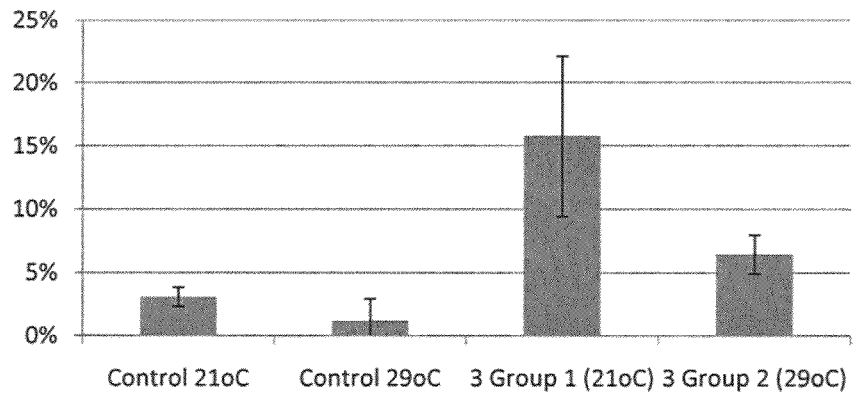
Fig. 8

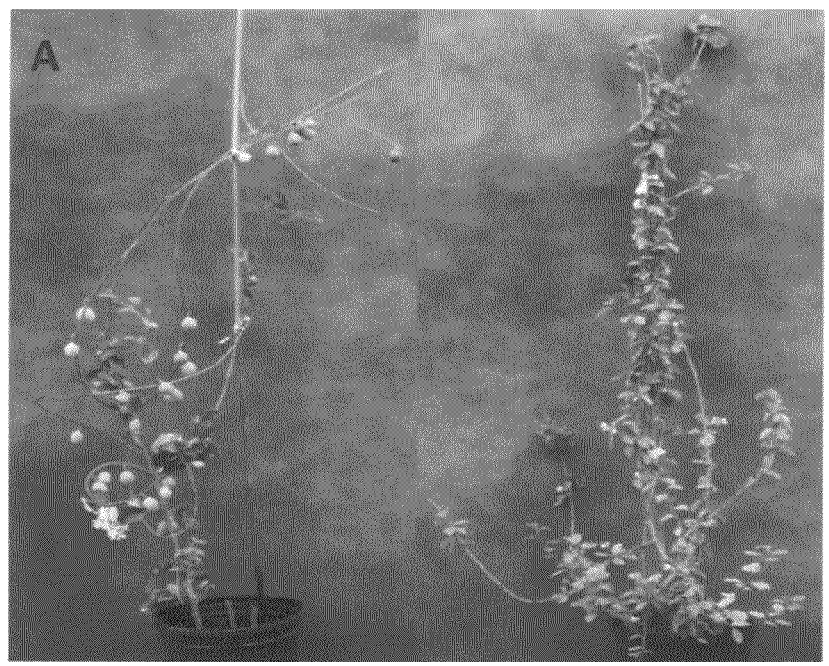
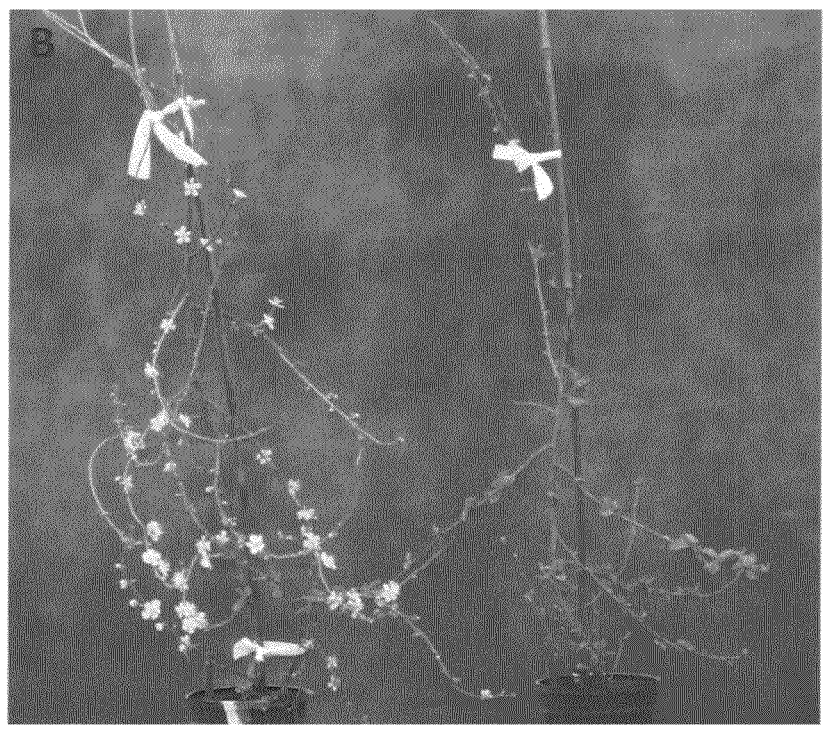
Fig. 9A-B

DEVELOPMENT OF VERY EARLY FLOWERING AND NORMAL FRUITING PLUM WITH FERTILE SEEDS

This application claims the benefit of U.S. Provisional Application No. 61/212,708, filed Apr. 15, 2009, which is incorporated herein by reference in its entirety.

BACKGROUND OF THE INVENTION

1. Field of the Invention

This invention relates to the development of transgenic plum genotypes which flower very early and continually and produce normal fruits and fertile seeds within six to twelve months and the seeds and plants obtained from such transgenic plants. The invention also relates to a method of transforming plum plant cells and plum plants utilizing a recombinant vector containing the construct comprising the gene for early flowering, PtFT1.

2. Description of the Relevant Art

*Prunus* is the horticulturally valuable genus in the family Rosaceae. Members of the family Rosaceae are cultivated for their fruits (peaches, plums, apricots, nectarines, cherries), nuts (almond) or for their ornamental flowers (flowering cherries). In addition to being a dietary supplement important for human health, *Prunus* fruits are a rich source of antioxidants which are widely reported to reduce cancer risks in humans. Conventional breeding and the application of molecular genetic technology such as structural and functional genomics and genetic engineering can be used to improve *Prunus* species. Currently, numerous genes in rosaceous fruit trees and related species have been identified through world-wide efforts of genome analyses (Retrieved from the Internet: <URL: bioinform.wsu.edu/gdr), but characterization of gene function through overexpression or gene silencing approaches in transgenic plants for genetic improvement of *Prunus* fruit trees is still problematic (Shulaev et al. 2008. *Plant Physiol.* 147: 985-1003).

Fruit tree breeding is a slow, arduous process that has changed little over the centuries. The long juvenile (preflowering) period of three to eight years is a severe impediment to the genetic improvement of both conventionally bred and transgenic *Prunus* fruit trees. Several generations of backcrossing and selection are required to develop improved *Prunus* cultivars; this process normally takes more than 20 years (Scorza, R. 2001. *HortScience* 36: 855-858). Limitations also include large land areas with significant field costs, and yearly limitations on flowering and fruiting related to chill and heat requirements. Shortening the 3-8 year juvenile period of *Prunus* fruit trees to a year or less by inducing early flowering in fruit trees could dramatically reduce the time, space and cost required for genetic improvement of fruit trees and result in the production of better quality fruits.

Tree fruits are temperate crops which are cultivated in orchard systems and require a period of chilling for continued growth and fruit production. They produce a single crop of fruit/nuts per year, the timing of which depends on the species and variety but is typically between the months of June and September. The amount of chill needed for each variety and the timing of flowering and fruit set impose significant barriers to where individual species and cultivars can be productively grown. This situation results in product surplus during summer months and a lack of product in the winter months but often filled by foreign imports. The ability to alter these crops such that they are no longer limited by time of chilling and/or extend the production season through continued flowering and fruit set would provide substantial improvements to crop productivity and market delivery.

Molecular genetics of flowering has been widely reported in the model plant and ectopically overexpressed flower-inducing genes have produced early flowering in *Arabidopsis* and other herbaceous plants. Through many studies in *Arabidopsis*, the pathway to flower determination has been resolved. Normally, there is an interaction between temperature and light which affects the levels of FLOWERING LOCUS C (FLC) and CONSTANS (CO), respectively. FLC negatively regulates FLOWERING LOCUS T (FT) and CO positively regulates FT. FT induces APETALA1 (AP1), FRUITFUL (FUL) and SUPPRESSOR OF CONSTANS OVEREXPRESSION 1 (SOC1), and SOC1 induces LEAFY (LFY). Other genes associated with flower induction include: FLOWERING LOCUS D (FD), and CAULIFLOWER (CAL). Overexpression of these genes individually or collectively and the silencing of TERMINAL FLOWER 1 (TFL1), can induce early flowering in *Arabidopsis* and other plants; for review, see Parcy, F. (2005. *Int. J. Dev. Biol.* 49: 585-593). LFY and AP1 determine flower meristems (Parcy, supra); AP1, LFY, FT and FUL have been used to shorten the juvenility period in trees resulting in early flowering. Several MADS-box genes also induce early flowering in plants. Since flowering is an essential process for the survival of plant species, floral-related gene redundancy is common. FT is now considered as the elusive flowering signal 'florigen'. Based on the current knowledge, it appears that FT protein produced in companion cells of phloem in small veins of leaves is translocated to shoot apical meristems where it activates the shoot apical meristem-specific transcription factor FD which in turn recruits the meristem-identity gene LFY and its homologs AP1 and CAL to induce flowering in plants (Abe et al. 2005. *Science* 309: 1052-1056; Parcy, supra; Wigge et al. 2005. *Science* 309: 1056-1059).

Several flower-inducing genes discovered in *Arabidopsis* have been tested in woody perennial plant systems. Some form of early flowering has been reported in apple, citrus, and poplar by overexpressing MADS4 and FT genes. Flachowsky et al. (2007a. *Acta Hort.* 738: 307-312) obtained an early flowering clone of the apple cultivar 'Pinova' by overexpressing a silver birch (*Betula pendula* Roth) floral meristem identity MADS-box gene, bpMADS4. These transgenic apple plants flowered within 13 weeks of transformation and initially produced solitary flowers, but later produced clusters of 5 flowers. Pollination of these flowers with *Malus fusca* pollen produced normal fruits and seeds (Flachowsky et al. 2007b. *Plant Breeding* 126: 137-145). In citrus, constitutive expression of citrus FT (CiFT) in trifoliated orange (*Poncirus trifoliate*) induced early flowering as early as 12 weeks after transfer of transgenic plants to a greenhouse (Endo et al. 2005. *Trans Res.* 14: 703-712). The transgenic lines showed variation in phenotypes such as time of first flowering and tree shape. Two FT genes have been isolated from poplar. PtFT1 has been isolated from *Populus trichocarpa* (Bohlenius et al. 2006. *Science* 312: 1040-1043) and PtFT2 is from *P. deltoides* (Hsu et al. 2006. *Plant Cell* 18: 1846-1861). Male poplar hybrid *P. tremula*×*P. tremuloides* flowered as early as four weeks post-transformation when overexpressing PtFT1, whereas PtFT2, which has 91% similarity in coding regions at the amino acid level, induced flowering after a year. It appears that PtFT2 is involved in seasonal flowering. Although early flowering has been achieved by overexpressing several MADS-box genes and transcription factors, these genes are multifunctional and overexpression of these genes induced alterations both in vegetative and reproductive growth and development. However, FT is neither a transcription factor nor a MADS-box gene and overexpression of FT did not adversely affect normal growth and development of plants (Bohlenius, supra).

The tree fruit industry is facing challenges of climate change, reductions in available labor, the need for reduced chemical inputs, and the spread of exotic pests and pathogens. To meet these challenges the development of improved varieties is vital. The objective of our research was to utilize the knowledge of the molecular genetics of flowering gained in *Arabidopsis* and to design and implement a strategy and model system to routinely induce early flowering and normal fruiting in *Prunus*.

SUMMARY OF THE INVENTION

We have ectopically expressed the isolated PtFT1 gene (SEQ ID NO:1) from poplar (*Populus trichocarpa*) in *Prunus domestica* and confirmed that its expression results in the induction of early and continual flowering and decreasing the long juvenile pre-flowering period in the transformed plants.

In accordance with this discovery, it is an object of the invention to provide a strategy and model system to routinely induce early and continual flowering and normal fruiting in *Prunus* using the poplar FT gene (PtFT1) in plum and to use the strategy for accelerating the *Prunus* breeding cycle to obtain new improved cultivars and for climate-independent and continual fruit production systems.

It is an object of the invention to provide transformed *Prunus* plant cells and *Prunus* plants which flower early and continually and have a shorter juvenile (pre-flowering) period wherein said plant cells and plants comprise a recombinant vector comprising the PtFT1 gene.

It is a further object of the invention to provide seeds obtained from the PtFT1 transgenic *Prunus* plants.

It is a still further object of the invention to provide a method of regulating time of flowering of a *Prunus* plant by ectopically overexpressing the PtFT1 gene in a *Prunus* plant and plant cells.

It is another object of the invention to provide a method of producing an early flowering plant comprising: constructing a recombinant vector comprising the PtFT1 gene, transforming *Prunus* plant cells with the recombinant vector, and regenerating a plant from the obtained transformant.

It is another object of the invention to provide a method of producing an early flowering plant that continually flowers and fruits and is not subject to environmental cues such as day length and/or cold-induced, heat-induced or any other environmentally or artificially-induced dormancy-promoting cues.

It is another object of the invention to provide a method of improving *Prunus* breeding to obtain new improved cultivars comprising: using a strategy for accelerating the *Prunus* breeding cycle by transforming *Prunus* plant cells with the recombinant vector comprising the PtFT1 transgene, obtaining transformants which flower early and continually and produce ripe fruits with fertile seeds, regenerating early and continually flowering PtFT1 *Prunus* plants from the obtained transformants, breeding the PtFT1 *Prunus* transformants to non-transformed *Prunus* plants to obtain improved varieties of plants, and selecting the plants that do not carry the PtFT1 transgene for use in conventional breeding.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 1A-1F depict branching and canopy architecture of the transgenic phenotype. FIG. 1A shows the highly branched and profuse flowering upright transgenic phenotype. FIG. 1B shows a one year old control 'BlueByrd' seedling showing few small lateral branches. FIG. 1C shows the canopy of an upright grown transgenic line. FIG. 1D shows the canopy of a partially upright phenotype. FIG. 1E shows the bushy phenotype. FIG. 1F shows the canopy architecture of the bushy phenotype. Leaves were removed from FIGS. 1B, 1C, and 1D to show the canopy architecture.

FIGS. 2A-2L depict flowering in the transgenic plants. FIG. 2A depicts flower bud formation from leaf axils of an in vitro produced plantlet. FIG. 2B depicts an in vitro-regenerated shoot showing a cluster of flower buds. FIG. 2C depicts flowering from in vitro-produced transgenic plantlets. FIG. 2D depicts multiple flowers produced from a plantlet. FIG. 2E shows an anther from an in vitro-produced flower showing pollen grains. FIG. 2F depicts the double pistils from an in vitro-produced flower. FIG. 2G shows leafy sepals in flowers produced in some greenhouse-grown transgenic line. FIG. 2H shows flowering in a rooted plantlet grown in a growth chamber. FIG. 2I depicts early flowering from lateral shoots of a transgenic line one month after planting in the greenhouse. FIG. 2J depicts development of flowers from old buds on the trunk of a transgenic plant in the greenhouse. FIG. 2K shows four kinds of flowering habits of the early flowering plum phenotype. FIG. 2L depicts a lateral shoot showing a single flower and terminal and axillary panicle of flowers.

FIGS. 3A-3F depict the development of ripe plum fruits. FIG. 3A shows the development of ripe plum fruits from a pot-grown transgenic plant 6 months after planting in the greenhouse. FIG. 3B shows multiple fruits from a flower. FIG. 3C shows control 'BlueByrd' plums from the orchard. FIG. 3D shows ripe plums developed from an early-flowered transgenic plant in the greenhouse. FIG. 3E depicts a longitudinally cut control plum. FIG. 3F depicts a longitudinally cut transgenic plum showing flesh and seed development. The insert shows the size of the control seed (upper) and the transgenic plum stone.

FIG. 4 depicts an early continually flowering plum plant in the greenhouse. FIG. 4A shows a mature crop on a 1-year old fruiting plant. FIG. 4B shows a close-up view of fruit of the plant of FIG. 4A. FIG. 4C depicts flowers and two fruits at different stages of development on this same plant, illustrating the continuous production of flowers and fruit on plants containing the PtFT1 gene construct. FIG. 4D depicts a flowering shoot on an 8-month-old plant.

FIGS. 6A and 6B depict three year old, greenhouse grown plum plants. FIG. 6A depicts a three year old FT plum plant with flowers and fruit that has never undergone vernalization. FIG. 6B depicts a similar aged standard plum tree that has nearly ceased growing after only one year in the greenhouse without vernalization.

FIG. 7 is an image showing flower panicles formed in FT plums.

FIGS. 8A-C show the effects of three weeks of growth at 21° C. or 29° C. for control plums (first two bars) and an FT plum line (2$^{nd}$ two bars) on flowering (FIG. 8A), on bud development (FIG. 8B) and on bud break (FIG. 8C).

FIGS. 9A and 9B show the effect of temperature on fruit retention. FIG. 9A shows fruit retention in plants shifted to 21° C. after 6 weeks of growth at 29° C. (left) vs. 21° C. (right). The plant on the left carries nearly 30 fruit while the plant on the right has none. FIG. 9B shows clones of the same FT plum line grown under 29° C. (left) vs. 21° C. (right) prior to vernalization.

DETAILED DESCRIPTION OF THE INVENTION

Figure 5:
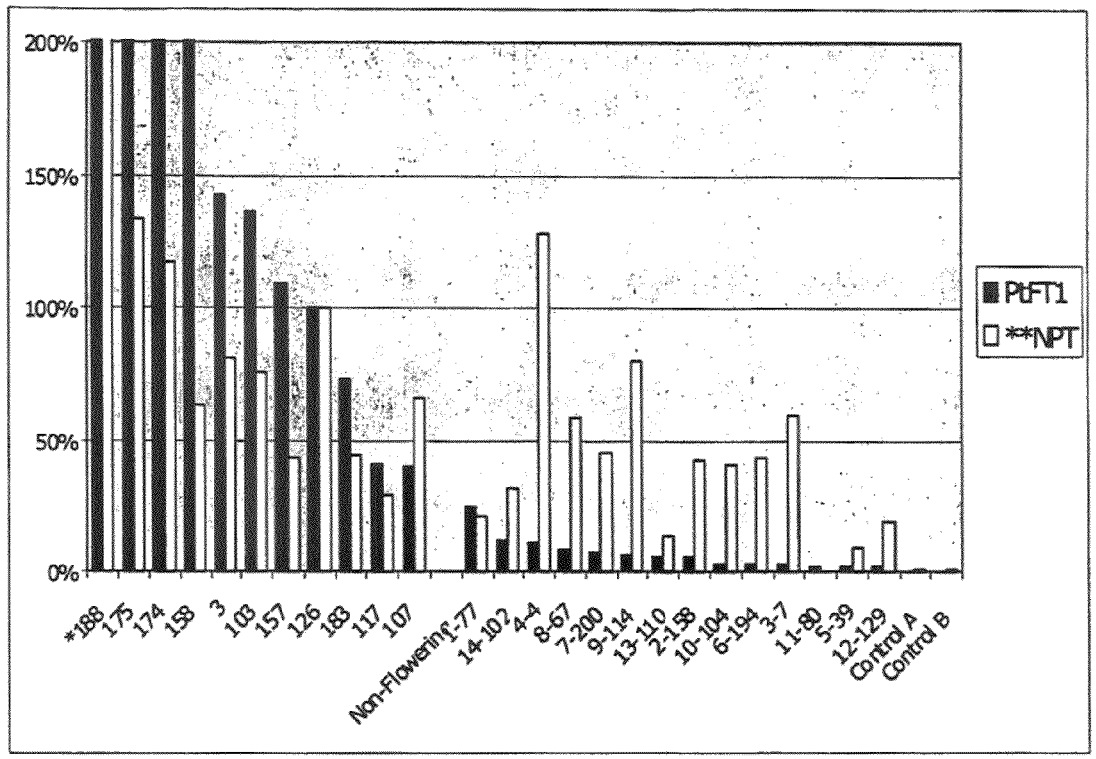
FIG. 5 depicts quantitative PCR analyses of RNA extracted from leaves sampled from flowering and non-flowering transgenic plants grown in the greenhouse. The histogram shows relative amounts of PtFT1 and NPTII transcripts in leaves as compared to transgenic line 126 anchored as 100%. Profusely flowering transgenic lines 3, 103, 158, 174, and 175 showed more transcripts as compared to non-flowering and intermittently flowering plants.
Figure 10:
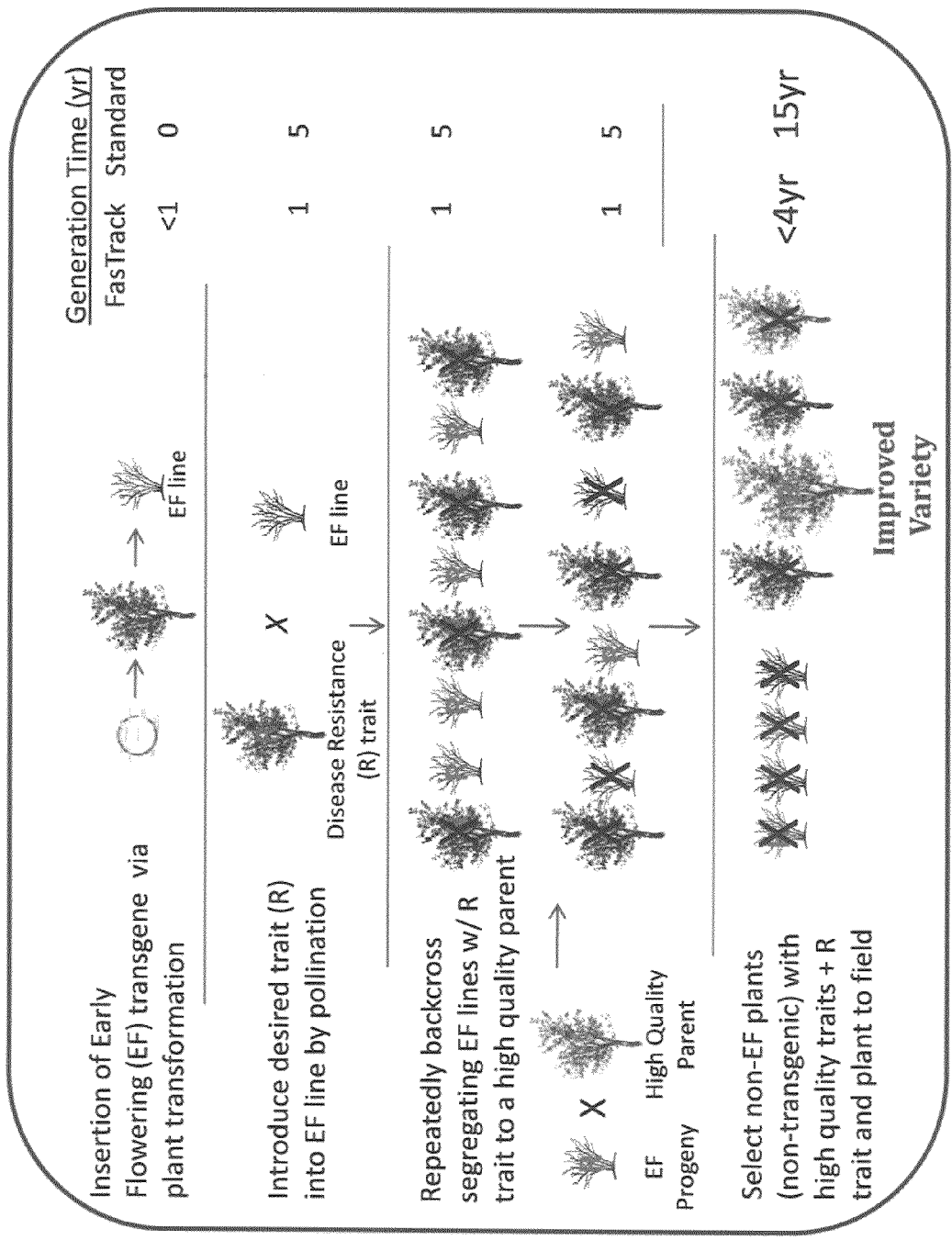
FIG. 10 illustrates a breeding scheme depicting the introgression of a single dominant disease resistance trait (R) from wild type germplasm with poor fruit quality to a high quality variety.

We have transformed Plum (*Prunus domestica* L) with the poplar (*Populus trichocarpa*) Flowering Locus T1 (PtFT1) gene encoding the PtFT1 polypeptide (SEQ ID NO:1; Nilsson et al. U.S. Patent Application 2008/0066198 Mar. 13, 2008). This invention concerns the first occurrence of induction of early flowering in a rosaceous species, *P. domestica* by ectopic expression of PTFT1. This regulation of flowering in *Prunus* enables a breeding system where the limitations of juvenile period are overcome and makes possible generation times in *Prunus* of one year versus the conventional 3-10 or more years breeding cycle.

Temperate tree fruit crops require a period of dormancy to induce flower formation and bear fruit. This attribute limits their cultivation to temperate zones with sufficient chilling hours. Production is absent in the winter months and can be over-abundant during the growing season exceeding the demand of the local market and making export of fresh product difficult, particularly for fruit with poor storage qualities. Recent climate models predict that by mid-century major temperature crop production regions will no longer experience sufficient chilling to support many fruit crops and new, adaptable systems for temperate tree fruit production will be needed.

Transgenic over-expression of the FT gene in *Prunus domestica* resulted in trees that changed from a temperate upright tree growth habit to a bush habit capable of continual fruit bearing without the need for a period of chilling. Flowering was altered such that, instead one or a few flowers, a stem with inflorescence clusters or panicles emerged from single buds much like grapes. FT plums did not respond to cold or daylength induced dormancy but remained winter hardy in the field. Also, floral bud set and flowering responded predictably to changes in temperature. Thus, by manipulating a single gene, temperate tree crops can be effectively engineered for cultivation in new growing areas and for entirely new modes of agricultural production that are continuous, sustainable, and adaptable to climate change.

Flowering in some transgenic lines began in vitro within 2 months following transformation. Other lines flowered within one month after planting in the growth chamber. Plants continued to flower following transfer to the greenhouse where additional plants flowered. The intensity of flowering was positively related to the expression level of PtFT1 mRNA. Flowers were generally fertile and produced normal fruit with viable seeds. Seedlings from these fruit also flowered in vitro due to constitutive high expression of PtFT1.

Plums usually initiate flowers in lateral buds of both the current season shoots as well as in the new growth of older spurs. Each bud contains 1-3 flowers and no leaves. All terminal buds are vegetative. However, PtFT1-expressing early flowering plum plants produced 1-3 axillary flower buds from leaf axils of current shoots. Terminal panicles of 4 to 8 flowers could be observed in the lateral shoots of PtFT1-expressing plants; this was not observed in control plum trees. The overexpression of the PtFT1 gene altered the natural flowering habit of plums by producing terminal and axillary panicles of flowers and multiple axillary flowers. Such alteration in the natural flowering habit due to overexpression of FT1, LEAFY and APETALA 1 genes has been reported in citrus (Pena et al. 2001. *Nature Biotech.* 197: 263-267; Endo et al., supra). Here, constitutive overexpression of the PtFT1 gene increased flowering and in some cases can convert almost all the shoot apical meristem into flowers. Even the hypocotyl sections excised from the overexpressing transgenic plum zygotic embryos, when cultured on shoot regeneration medium may in some cases regenerate flower buds instead of adventitious shoots. Flowering in vitro can be controlled by manipulation of the in vitro growth medium. In vitro flowering of PtFT1 expressing plantlets can be prevented by culturing in modified Quoirin and LePoivre medium containing high nitrogen and cytokinin (Quoirin and LePoivre. 1977. *Acta Hortic.* 78:437-442).

Although the PtFT1 gene was driven by a constitutive promoter, the flowering initially occurred only in 20 percent of the plants which had accumulated comparatively high FT transcripts (FIG. 5). A similar large increase in FT1 transcript prior to flower induction has been widely reported in other woody perennial plants such as grapevine (Carmona et al. 2002. *Plant Physiol.* 130: 68-77), apple (Wada et al. 2002. *Plant Mol. Biol.* 49: 566-577; Hattasch et al. 2008. *Tree Physiol.* 28:1459-1466), and poplar (Hsu et al., supra). The transition from juvenile single stemmed plum seedling to a well-branched flowering adult tree takes 3 to 4 years (Scorza, supra), but constitutive expression of the poplar FT1 gene in the transgenic plum plants produced several lateral branches and flowers within a month of planting in the greenhouse. This indicates that the role of the FT1 gene is not only to induce flowering, but it appears that the FT1 gene is involved in the phase change from juvenile to adult phase.

At a morphological level, the combination of phenotypes in FT plums rendered them distinctly different from typical *Prunus* species but whether or not they were capable of normal environmental transitions was not apparent. A hallmark of temperate tree crops is their dependence on seasonal cycles for growth and reproduction. Flowering is brought about by warm spring temperatures and increased day length. Then, during the long days and warm temperatures of summer, trees enter a vegetative growth phase during which time new flower buds are set and the trees accumulate energy stores for winter. Cool weather and shortened day lengths in fall promote the onset of dormancy which is associated with terminal bud set, growth cessation, and freezing tolerance. We evaluated FT plums to determine if they could still respond to changing environmental conditions and/or undergo dormancy.

While further studies will be necessary to elucidate the effects of PtFT1 on plum tree and flower morphology, the induction of early and continual flowering and the production of ripe fruit with fertile seeds within a year from the time of transformation presents an important genetic tool to reduce the generation interval of plum and other rosaceous fruit crops. It will facilitate rapid functional analyses of genes involved in fruit development and can be used to drastically shorten the hybridization-based breeding cycle.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985.

A "construct" or "chimeric gene construct" refers to a nucleic acid sequence encoding a protein, here the PtFT1 protein, operably linked to a promoter and/or other regulatory sequences.

As used herein, the term "express" or "expression" is defined to mean transcription alone. The regulatory elements are operably linked to the coding sequence of the PtFT1 gene such that the regulatory element is capable of controlling expression of PtFT1 gene. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. The tissue-specificity of a promoter, for example, is exemplified by the promoter sequence (described above) which specifically induces gene expression in root tips. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

A "protein" or "polypeptide" is a chain of amino acids arranged in a specific order determined by the coding sequence in a polynucleotide encoding the polypeptide. Each protein or polypeptide has a unique function.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

The successful transformation of *Prunus* with PtFT1 is a major step in overcoming generation time in fruit trees and will aid in devising new strategies for improving breeding in *Prunus*, thus ensuring the development of improved varieties of *Prunus*.

The creation of plum trees that do not undergo dormancy and produce flowers and fruit continually offer new strategies for growing and producing *prunus* fruits/nuts in a fashion that is continual and climate-independent and will provide a more stable and continuous supply of these products and their derivatives.

EXAMPLES

Having now generally described this invention, the same will be better understood by reference to certain specific examples, which are included herein only to further illustrate the invention and are not intended to limit the scope of the invention as defined by the claims.

Example 1

Transformation

The plasmid pK2GW7 containing the Cauliflower Mosaic Virus 35S (CaMV 35S) promoter, and nptII and PtFT1 genes (Nilsson et al., supra) were transformed into the *Agrobacterium tumefaciens* strain GV3101. Hypocotyl sections excised from surface-sterilized mature seed embryos of plum cultivar 'BlueByrd' were transformed with *A. tumefaciens* strain GV3101 containing the 35S::PtFT1 gene (Bohlenius et al., supra). The transformed hypocotyl sections were cultured in vitro and transgenic plants were regenerated and rooted as described in Petri et al. (2008. *Mol. Breeding* 22:581-591). The rooted plantlets were acclimated in the growth chamber (20° C.; light intensity 70 μmol photons $m^2s^{-1}$, 16 h light/8 hr dark photoperiod) for 2-3 weeks and planted in 6 or 9 inch pots and grown in a temperature controlled (27° C.) glasshouse under sunlight during the months of December 2007 to November 2008 to evaluate flowering and fruit production.

Example 2

Transgenic Plants: Vegetative and Flowering Characteristics

The presence of 35S::PtFT1 gene in plum was determined by PCR analyses of DNA extracted from leaves using the published primers (Bohlenius et al., supra). A total of 196 transgenic plum plants representing 56 transgenic clones were regenerated. Flowering was scored in vitro, in the growth chamber, and in the greenhouse. Since 'BlueByrd' plum is self incompatible, pollen from compatible plum cultivars 'Stanley' or Cacanska Lepotica' was used to pollinate the transgenic plum flowers in the greenhouse. Fully ripe plum fruits were evaluated for size, color, brix, and stone and seed development. Viability of transgenic seed embryos was determined by culturing embryo shoot tips and hypocotyls sections following the tissue culture methods of Petri et al. (supra) without the use of antibiotic selection.

Extensive lateral shoot production was observed in all transgenic plants within 6 months of planting in the greenhouse (FIG. 1, Table 1). Non-transgenic control plants produced few small lateral shoots even after a year of growth (FIG. 1B). While most transgenic plants were branched and grew upright (FIGS. 1A and 1C), some transgenic plants showed a combination of upright and bushy growth (FIG. 1D). Still others of the transgenic plants were bushy and recumbent resembling a ground cover plant due to early lateral branching and the lack of apical dominance of the main shoot (FIGS. 1E and 1F). Unlike flowering, profuse lateral branching occurred even in plants which expressed low levels of PtFT1 transcript.

TABLE 1

Production of lateral shoots and flowers in PtFT1-expressing transgenic plum plants after 10 months of growth and development in nine inch pots under the greenhouse conditions.

| Transgenic Line | Flowering Time In Months | Number of Lateral Shoots | Number of Flowers Per Leaf Axil | | | |
|---|---|---|---|---|---|---|
| | | | 1 | 2 | 3-5 | Terminal Panicle |
| A. Upright and Semi-upright Phenotypes | | | | | | |
| 3 | 4 | 28 | 109 | 32 | 18 | 17 |
| 16 | 9 | 18 | 2 | 0 | 0 | 0 |
| 27 | 10 | 12 | 4 | 3 | 2 | 0 |
| 29 | 8 | 16 | 8 | 1 | 2 | 0 |
| 32 | 8 | 18 | 4 | 2 | 0 | 0 |
| 33 | 10 | 15 | 1 | 0 | 0 | 0 |
| 34 | 7 | 27 | 83 | 23 | 4 | 2 |
| 51 | 10 | 11 | 1 | 0 | 0 | 0 |
| 52 | 10 | 11 | 1 | 0 | 0 | 0 |
| 73 | 8 | 17 | 2 | 1 | 0 | 0 |
| 74 | 9 | 15 | 0 | 0 | 3 | 0 |
| 76 | 8 | 10 | 1 | 4 | 1 | 0 |
| 88 | 8 | 16 | 4 | 3 | 1 | 0 |
| 90 | 7 | 17 | 6 | 3 | 0 | 0 |
| 91 | 7 | 21 | 4 | 3 | 0 | 0 |
| 103 | 1 | 33 | 79 | 52 | 53 | 21 |
| 117 | 6 | 12 | 4 | 2 | 1 | 0 |
| 118 | 7 | 11 | 2 | 5 | 0 | 0 |
| 119 | 10 | 14 | 2 | 0 | 0 | 0 |
| 139 | 10 | 11 | 5 | 4 | 2 | 0 |
| 140 | 7 | 18 | 5 | 3 | 1 | 0 |
| 147 | 7 | 13 | 2 | 0 | 0 | 0 |
| 148 | 7 | 11 | 2 | 2 | 0 | 0 |
| 152 | 7 | 12 | 4 | 2 | 0 | 0 |
| 157 | 5 | 26 | 24 | 11 | 12 | 4 |
| 175 | 7 | 19 | 3 | 2 | 1 | 0 |
| 183 | 5 | 13 | 8 | 3 | 0 | 0 |
| 187 | 6 | 18 | 1 | 2 | 1 | 0 |
| 188 | 6 | 16 | 3 | 1 | 0 | 0 |
| 189 | 6 | 6 | 3 | 0 | 0 | 0 |
| 192 | 7 | 12 | 5 | 0 | 0 | 0 |
| 193 | 7 | 13 | 3 | 0 | 0 | 0 |
| B. Bushy Phenotypes | | | | | | |
| 52 | 7 | 15 | 2 | 1 | 0 | 0 |
| 107 | 7 | 23 | 4 | 1 | 0 | 0 |
| 126 | 6 | 32 | 5 | 7 | 0 | 0 |
| 141 | 6 | 12 | 3 | 0 | 0 | 0 |
| 158 | 6 | 28 | 18 | 12 | 3 | 3 |
| 174 | 5 | 21 | 31 | 22 | 8 | 3 |
| 222 | 7 | 9 | 1 | 1 | 0 | 0 |
| 223 | 8 | 14 | 7 | 1 | 0 | 0 |

The FT plum shrub habit appeared to be the result of three characteristics: 1) Loss of apical dominance that was sometimes, but not always, due to the production of a terminal inflorescence, 2) lateral branches tended to have weaker attachment sites and repeatedly cracked and re-healed eventually resulting in downward branch angles, and 3) the trunk and lateral branches did not grow straight and instead curved. Second, FT plum lines grew continuously and did not consistently set terminal buds unlike non-transformed control trees that undergo growth cessation as day lengths become shorter. Some FT plum lines continued to grow, flower, and produce fruit even after 3 years at 65-85° C. in a temperature controlled greenhouse.

Although lateral branching occurred even at a low level of PtFT1 gene expression, induction of flowering requires accumulation of more than a certain threshold level of FT1 transcript. Flower buds were produced in vitro from about four percent of transgenic plum plantlets within two months of transformation. Few in vitro-produced flower buds produced fully developed flowers with normal calyx, corolla and pollen-bearing anthers, but they had 2-4 pistils (FIGS. 2A-2C). Up to three flower buds developed from each leaf axil (FIG. 2A). Clusters of flower buds developed from some shoots (FIG. 2B), but these flower bud clusters atrophied without developing further. Most of the in vitro flowering plantlets lacked vegetative shoot meristems and therefore could not be rooted and planted in the soil for further evaluation. Plants that did not flower in vitro were rooted and transferred to the growth chamber (400μ Einstein light intensity; 16/8 photoperiod; 21-24° C. temperature; 75% humidity) where six plants flowered within a month of being transferred to the growth chamber. These produced normal flowers, but these flowers did not set fruits probably due to lack of cross pollination (FIG. 2H). Up to five flowers were produced per plantlet (FIG. 2D).

Following transfer to the greenhouse 20.9% of plants (41 plants out of 196 plants planted) flowered between 1 month (FIG. 2I) and 10 months after planting in the greenhouse (FIGS. 1A and 1E, Table 1). The temperature in the glass house varied from 24 to 27° C. and the light was natural sun light. These included those plants that had flowered in the growth chamber. The frequency of flower formation varied. Of the 41 flowering plants from 56 lines, five plants (transgenic lines 3, 103, 34, 158, and 174) produced flowers profusely for 4-6 weeks, while others produced few flowers sporadically for 6 weeks (Table 1). Accumulation of PtFT1 transcript in leaves was high in profusely flowering plants as compared to sparsely flowering plants. Non-flowering PtFT1 plants accumulated the lowest levels of transcript in leaves.

Flowers generally formed in the leaf axils of lateral shoots (FIGS. 2I and 2L). The number of flowers per leaf axil varied from 1 to 3 (FIG. 2K, Table 1). Some leaf axils bore both vegetative and flower buds. In addition to axillary flowers, lateral shoots often produced a terminal panicle of 4 to 8 flowers (FIGS. 2K and 2L). Most flowers had 5 sepals, 5 petals, 16 to 23 anthers and 2 to 4 pistils (FIGS. 2E and 2F). Flowers also appeared from old buds on the trunk. These flowers also produced fruits following hand pollination (FIG. 2J). The majority of flowers showed normal morphology with the exception of a higher number of pistils per flower (FIGS. 2H, 2K, and 2L); however, a few flowers were abnormal, i.e., they had leafy overgrown sepals (FIG. 2G) or malformed petals, 4, 6, or 7 petals or few anthers.

A total of 32 plum fruits were produced in the greenhouse by hand pollinating the flowers in the profusely flowering transgenic lines. Pollination of multiple pistils produced up to 3 ripe fruits per flower (FIG. 3B). Plum fruits in the greenhouse-grown transgenic plants developed normally and ripened 5 months after fruit set. Ripe fruits displayed red purple skin color (FIG. 3D; Table 2) and greenish-yellow flesh color (FIG. 3F). Fruits were smaller than the fruits produced from plum trees grown in the orchard (FIGS. 3C and 3D). The size of fruits varied from 10 to 37 mm in length and 5 to 34 mm in diameter (Table 2a, b). Early continually flowering 1-year old fruiting plants produce mature fruit crops in the greenhouse. Flowers and fruits at different stages of development are found on the same plant (FIG. 4C). Brix of fruit juice varied from 8 to 11°.

TABLE 2a

Characteristics of fruits, stones, and seeds harvested from an orchard-grown control plum tree and from the pot-grown PtFT1-expressing transgenic plum plants in the greenhouse.

| Transgenic Line | Fruit (mm) | | Stone (mm) | | Seed (mm) | | Brix | Fruit Color* | |
|---|---|---|---|---|---|---|---|---|---|
| | L | D | L | W | L | W | Degree | External | Internal |
| Control | 44.8 | 37.8 | 27.2 | 14.8 | 16.2 | 10.4 | 15.6 | Violet | Green-Yellow |
| 3 | 31.7 | 29.1 | 14.4 | 7.2 | 10.0 | 5.0 | 10.5 | Blue 106B | Green-Yellow |
| 103 | 36.8 | 33.8 | 16.8 | 9.3 | 14.4 | 8.2 | 9.9 | Blue 106D | Green-Yellow |

* Fruit Color was determined by using Royal Horticultural Society Color Chart, UK
L—Length;
D—Diameter;
W—Width TABLE 2b Characteristics of fruits, stones, and seeds harvested from an orchard-grown control plum tree and from the pot-grown PtFT1-expressing transgenic plum plants in the greenhouse.

| Transgenic Line | Number of Fruits | Fruit Diameter mm | Fruit Weight gm | Brix |
|---|---|---|---|---|
| Control | 5 | 37.8 | 45.0 | 15.6 |
| #3 | 18 | 28.5 | N.D. | 13.1 |
| #29 | 6 | 30.1 | 18.1 | 11.5 |
| #32 | 3 | 30.0 | 15.3 | Mealy, no juice |
| #34 | 3 | 33.3 | 21.6 | 12.3 |
| #88 | 1 | 37.0 | 33.9 | mealy |
| #90 | 2 | 31.0 | 16.9 | 11.8 |
| #91 | 9 | 34.7 | 25.1 | 12.0 |
| #103 | 9 | 31.8 | ND | 10.2 |
| #152 | 1 | 28.0 | 13.4 | 10.8 |
| #157 | 21 | 31.0 | 17.0 | 10.4 |

N.D. Not Determined

Stones and seeds developed normally, but they were smaller than the orchard-grown plum seeds (FIG. 3F insert). Embryos excised from the seeds of early fruiting transgenic plums readily germinated in vitro. The hypocotyl sections excised from transgenic seed embryos regenerated adventitious shoots in vitro when the regeneration protocols of Petri et al. (supra) were utilized, without antibiotic selection. Some of these adventitious shoots and seedlings also produced flower buds in vitro, but these flower buds seldom develop into flowers. However, high levels of PtFT1 expression appeared to affect formation of vegetative meristem in the succeeding generation of transgenic plants developed from seed of profusely flowering lines. When the shoot apices of profusely flowering and fruiting transgenic lines, i.e., PtFT lines 3, 34, 103, and 157, were cultured, most of the in vitro-multiplied shoots produced up to 10 flowers per plantlet and these plants had few vegetative meristems. Rooting of these plantlets was also slow compared to control plantlets.

Alternatively, seeds were extracted from the stony endocarp by cracking open the endocarp. Seeds were then soaked in a 1.2% solution of Sodium hypochlorite for 20 min to 2 hrs then soaked in a solution of 500 ppm benzyladenine and 500 ppm gibberellic acid for 8-16 hrs. The seed coat may then be stripped off, but it is not necessary to strip off the seed coat. Seeds germinate within days of this treatment, thus avoiding a lengthy stratification requirement (200-1500 hrs at 4° C.) that *Prunus* seed normally need for germination. This procedure also avoids the need for in vitro culture of embryos.

Example 3

Transgenic Plants: Effects of Induced Dormancy

Three FT plum lines were clonally propagated and placed in environmental growth chambers with non-transgenic controls at either 21° C. or 29° C. for 8 weeks. Growth rate, node number, bud development or formation, bud break, and flower number were measured at 2 week intervals (FIG. 8). Data showed that growth rate, node number, and rates of bud break were similar in both temperatures but both node number and bud break were higher for FT lines relative to controls. In contrast, flowering was more prolific in FT plums at 21° C. while higher numbers of floral buds were set at 29° C. To confirm the temperature effect, after 8 weeks five plants were swapped from each chamber. Again flowering increased in plants shifted to 21° C. and was repressed at 29° C. Abnormal flowers only developed at 29° C. even in buds set at 21° C. suggesting that de-differentiation occurred post bud break.

Figure 11:
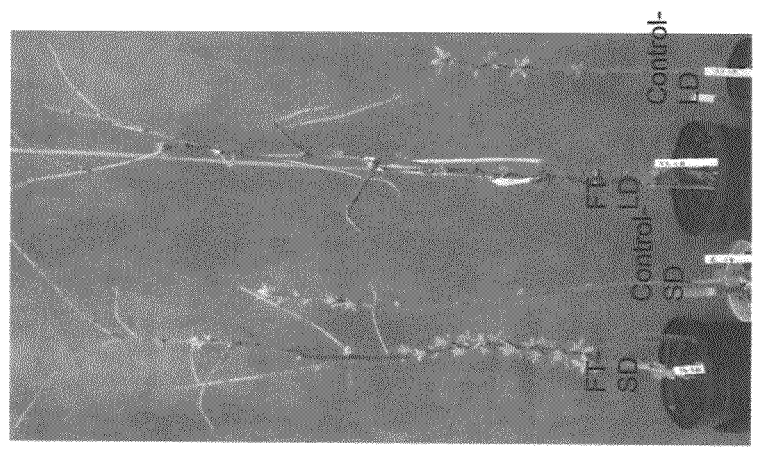
FIG. 11 illustrates the short day insensitivity of FT plums.

FT plums grown in the greenhouse were insensitive to short days during the winter months and did not undergo growth cessation. A controlled experiment was performed for FT plums in the growth chamber under short (8 hr) and long (16 hr) day lengths. After six weeks growth rate, bud set, bud break, and flower number were measured and showed no significant difference between the two light regimes unlike control plums which showed decreased growth rate under short days (FIG. 11).

Figure 12:
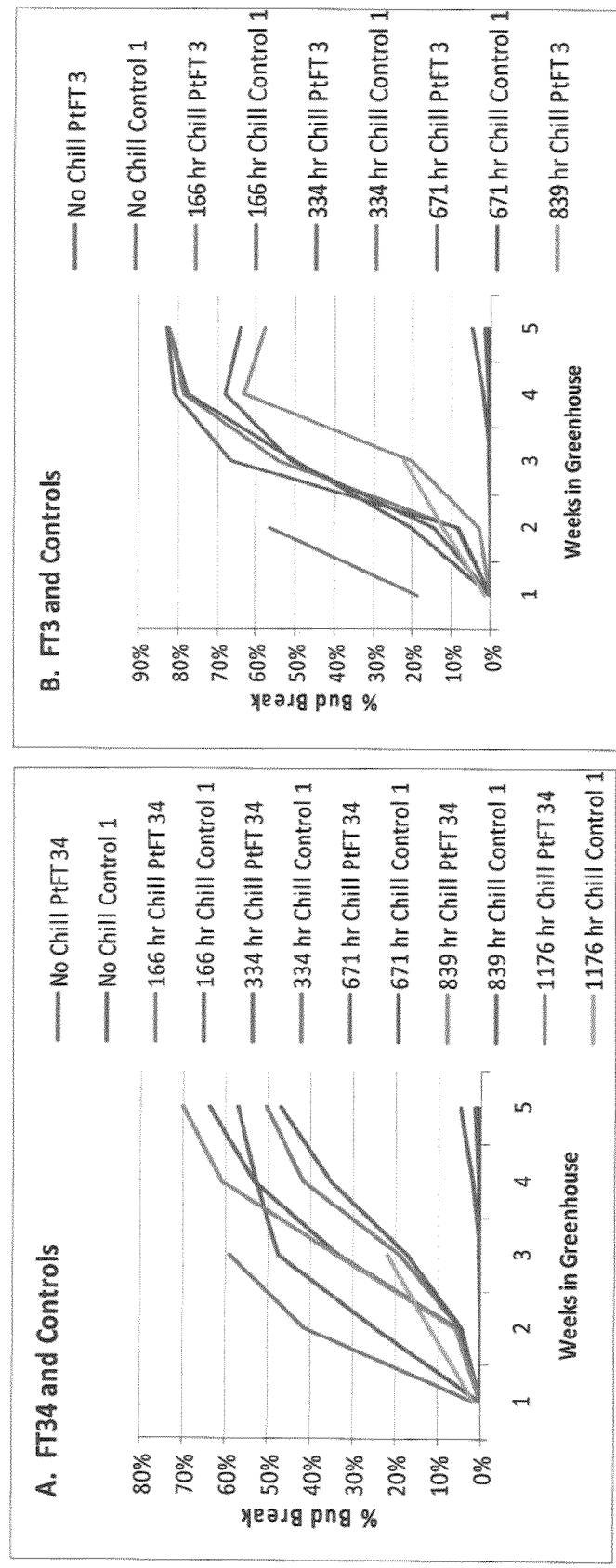
FIG. 12 illustrates the lack of chill requirement of FT plums.

Dormancy is a complex state and occurs as a consequence of diverse signaling pathways. A key characteristic of dormant temperate trees is the requirement for a sufficient number of chilling hours (defined as hours exposed to 0-7° C.) before efficient vernalization can occur. Chilling time varies among species and cultivars but for *P. domestica* a minimum of 800-1,000 chilling hours is typically required. We tested clonally propagated individuals from two FT plum lines along with an equal number of controls. Plants were placed in cold storage at 5° C., moved to the greenhouse at one week intervals, and the time to bud break was measured. Results showed that cold temperature treatment lead to a marked delay in bud break in control trees but not in FT plums (FIG. 12).

While laboratory experiments indicated that FT plums could respond normally to environmental cues and enter dormancy, we wanted to test whether they could survive a natural winter environment. Four plants each from two different FT plum lines along with controls were planted in field plots in late summer 2009. In late January, bud sticks were removed and checked for bud survival rates. Line #34 had 100% survival while line #3 was 84%. In spring 48 out 50 FT plum lines survived and resumed growth.

Example 4

RNA Extraction

One leaf punch from a single paper punch was collected from three different fully expanded, non-waxy leaves from one plant and pooled into one sample (~10 mg total), frozen in liquid nitrogen and stored at −80° C. until processed. All the leaf samples for one experiment were collected between 13:00 and 14:30 of the same day. RNA was extracted from the leaf material using the MagMAX-96 Total RNA Isolation Kit (Applied Biosystems, Foster City, Calif.) with some modifications to the protocol. Basically 100 µl of Lysis/Binding Solution was added to the sample along with ¼ amount of Lysing Matrix D (BIO 101 Systems, Thermo Scientific, Waltham, Mass.) and processed in a FastPrep (FP120, BIO 101, Thermo Scientific) bead beater for 27 sec at a 5 speed setting. The beaded material was spun first, and then the supernatant was placed in a clean microcentrifuge and processed as described in the manufacturer's protocol except that two washes were performed at each step. Three µl of the RNA was evaluated on a gel.

Example 4

Quantitative Real-Time PCR

Quantitative Real-time PCR (qRT PCR) was performed on the RNAs utilizing a one-step protocol with RNAse Inhibitor (Applied Biosystems), MuLv Reverse Transcriptase (Applied Biosystems) and SYBRGreen PCR Master Mix (Applied Biosystems) following the manufacturer's protocol. Initially, all the RNAs were run as a single reaction with either primers for chlorophyll A/B binding protein or the PFT transgene, with and without the RT, in order to verify the lack of significant DNA contamination. To determine the relative levels of RNA expressed, the RNAs were diluted (0.33 µl/reaction), and run in triplicate in 10 µl reactions on an ABI7900 (ABI). Primer sequences are listed in Table 3. All RNAs were also run with 26S primers at an additional 1000 fold dilution to determine the relative amount of each RNA in the reactions. A standard curve was run in triplicate with each primer set to determine the relative amounts. The results of the triplicate reactions were averaged and normalized by the relative amount of 26S RNA. To keep all the numbers on the same scale, the level of expression of line 126, the low flowering line, was set at 100% and all the other lines were compared to that line.

TABLE 3

Primer Sequences used:

| PRIMER | SEQUENCE | SEQ ID NO: |
|---|---|---|
| 1PtFT1-5' | CAGAACTTCAACACCAGAGA | 3 |
| 1PtFT1-3' | TCCTACCACCAGAGCCACT | 4 |
| 2PtFTb-5' | TTCTACACTCTGGTTATGGTGGACC | 5 |
| 2PtFTb-3' | GTTGCCGAAACAAGACGAAAAC | 6 |
| 326S-5' | GCAGCCAAGCCTTCATAGCG | 7 |
| 326S-3 | GTGCGAATCAACGGTTCCTC | 8 |
| 42057-5' | GTGTTCAGACCACTTCCTTCATCC | 9 |
| 42057-3' | CCATCTTCAACCTTCGGCTTC | 10 |
| 54040-5' | CAAGGCAACTACAACTCAGGCAG | 11 |
| 54040-3' | AGGCATCCCATACATAACACCAAG | 12 |

1 PtFT1 (415-517) Bohlenius et al. 2006. *Science* 312: 1040.
2 Designed from Acc# DQ387859 (187-379)
3 Previously published (Moon and Callahan. 2004.)
4 Wu et al. 2006. Genetics 174: 1407-1420. Designed from Contig 2057 in the Prunus Assembly V4 http://www.bioinfo.wsu.edu//cgi-bin/gdr/gdr_EST_contig_search.cgi?genus=*Prunus*.
5 As above, but from Contig 4040.

The ability of FT plums to continuously produce fruit irrespective of day length or chilling time and still survive extreme cold suggests they could be grown in both tropical and temperate climates. Their shrub growth habit and continual fruiting makes them suitable for non-orchard production systems either in the field or protected facilities where artificial changes in light and temperature could be used to manipulate growth and maximize fruit production to meet off season demand. Thus, FT plums represent an important milestone in temperate tree fruit biotechnology and pave the way for future advances to address the challenges facing temperate tree crop agriculture.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method of making early and continually flowering *Prunus* plants, said method comprising:
   a.) transforming a regenerable tissue of a *Prunus* plant with a recombinant construct comprising a *Populus trichocarpa* Flowering Locus T1 (PtFT1) cDNA and one or more regulatory elements operatively linked to said cDNA wherein said PtFT1 cDNA encodes the polypeptide of SEQ ID NO:2 or with a vector comprising said recombinant construct;
   b.) culturing the transformed *Prunus* plant regenerable tissue in vitro;
   c.) regenerating from said transformed *Prunus* plant regenerable tissue transgenic *Prunus* plantlets;
   d.) rooting said transgenic *Prunus* plantlets;
   e) acclimating said rooted transgenic *Prunus* plantlets in a growth chamber;
   f.) planting said acclimated transgenic *Prunus* plantlets in a temperature controlled greenhouse; and
   g.) selecting for a growing transgenic *Prunus* plant comprising said recombinant construct and exhibiting an early and continually flowering phenotype.

2. The method of claim 1 wherein said one or more regulatory elements of said recombinant construct is a constitutive promoter operably linked to said cDNA.

3. The method of claim 1 wherein said one or more regulatory elements of said recombinant construct is the CaMV 35S promoter.

4. The method of making early and continually flowering transgenic *Prunus* plants of claim 1, wherein said transgenic *Prunus* plant exhibiting an early and continually flowering phenotype also exhibits extensive lateral shoot production when compared to a non-transgenic control plant.

5. The method of making early and continually flowering transgenic *Prunus* plants of claim 1, wherein said transgenic *Prunus* plant exhibiting an early and continually flowering phenotype also exhibits a branched, upright growth pattern, a combination of branched, upright and branched, bushy growth pattern, or a combination of branched, bushy and branched, recumbent growth pattern when compared to a non-transgenic control plant.

6. A method of making an early and continually flowering transgenic *Prunus* plant wherein said transgenic *Prunus* plant exhibiting an early and continually flowering phenotype also produces ripe fruits with fertile seeds, said method comprising:
   a.) transforming a regenerable tissue of a *Prunus* plant with a recombinant construct comprising a *Populus trichocarpa* Flowering Locus T1 (PtFT1) cDNA and one or more regulatory elements operatively linked to said cDNA wherein said PtFT1 cDNA encodes the polypeptide of SEQ ID NO:2 or with a vector comprising said recombinant construct;
   b.) culturing the transformed *Prunus* plant regenerable tissue in vitro;
   c.) regenerating from said transformed *Prunus* plant regenerable tissue transgenic *Prunus* plantlets;

d.) rooting said transgenic *Prunus* plantlets;
e.) acclimating said rooted transgenic *Prunus* plantlets in a growth chamber;
f.) planting said acclimated transgenic *Prunus* plantlets in a temperature controlled greenhouse;
g.) selecting for a growing transgenic *Prunus* plant comprising said recombinant construct and exhibiting an early and continually flowering phenotype;
h.) pollinating transgenic *Prunus* flowers on said growing transgenic *Prunus* plant with pollen from compatible *Prunus* cultivars; and
i.) selecting for a growing transgenic *Prunus* plant comprising said recombinant construct and exhibiting an early and continually flowering phenotype and producing ripe fruits with fertile seeds.

7. The method of claim 6 wherein said growing transgenic *Prunus* plant grows, flowers, and produces fruit continuously for at least as long as three years.

8. The method of making a growing transgenic *Prunus* plant exhibiting an early and continually flowering phenotype and also producing ripe fruits with fertile seeds of claim 6 wherein said growing transgenic *Prunus* plant exhibiting the early and continually flowering phenotype and also producing ripe fruits with fertile seeds also exhibits a branched, upright growth pattern, a combination of branched, upright and branched, bushy growth pattern, or a combination of branched, bushy and branched, recumbent growth pattern when compared to a non-transgenic control plant.

9. A method of accelerating the breeding cycle of transgenic *Prunus* as compared to the breeding cycle of non-transgenic *Prunus* in order to provide continual, year round transgenic *Prunus* breeding to obtain new improved cultivars comprising:
   a.) transforming a regenerable tissue of a *Prunus* plant with a recombinant construct comprising a *Populus trichocarpa* Flowering Locus T1 (PtFT1) cDNA and one or more regulatory elements operatively linked to said cDNA wherein said PtFT1 cDNA encodes the polypeptide of SEQ ID NO:2 or with a vector comprising said recombinant construct;
   b.) culturing the transformed *Prunus* plant regenerable tissue in vitro;
   c.) regenerating from said transformed *Prunus* plant regenerable tissue transgenic *Prunus* plantlets;
   d.) rooting said transgenic *Prunus* plantlets;
   e.) acclimating said rooted transgenic *Prunus* plantlets in a growth chamber;
   f.) planting said acclimated transgenic *Prunus* plantlets in a temperature controlled greenhouse;
   g.) selecting for a growing transgenic *Prunus* plant comprising said recombinant construct and exhibiting an early and continually flowering phenotype;
   h.) pollinating transgenic *Prunus* flowers on said growing transgenic *Prunus* plant with pollen from compatible *Prunus* cultivars;
   i.) selecting for a growing PtFT1 transgenic *Prunus* plant exhibiting an early and continually flowering phenotype and producing ripe fruits with fertile seeds comprising said recombinant construct; and
   j.) germinating said seeds to produce PtFT1 transgenic *Prunus* plants comprising said recombinant construct and exhibiting an early and continually flowering phenotype and also bearing fully ripe *Prunus* fruit with fertile seeds thus providing continual, year-round transgenic *Prunus* breeding to obtain new improved cultivars and thereby exemplifying an accelerated breeding cycle for PtFT1 transgenic *Prunus* as compared to non-transgenic *Prunus*.

10. The method of claim 9 further comprising:
crossing early and continually flowering PFT1 transgenic *Prunus* plants of step (j.) to non-transformed *Prunus* plants to obtain new improved varieties of plants.

11. A method of obtaining new improved cultivars or varieties of *Prunus* exhibiting new characteristics in a shorter time period than is possible under conventional breeding conditions where crosses are made between non-PtFT1 transgenic *Prunus* plants for the purpose of obtaining new improved cultivars of *Prunus* comprising:
   a.) transforming a regenerable tissue of a *Prunus* plant with a recombinant construct comprising a *Populus trichocarpa* Flowering Locus T1 (PtFT1) cDNA and one or more regulatory elements operatively linked to said cDNA wherein said PtFT1 cDNA encodes the polypeptide of SEQ ID NO:2 or with a vector comprising said recombinant construct;
   b.) culturing the transformed *Prunus* plant regenerable tissue in vitro;
   c.) regenerating from said transformed *Prunus* plant regenerable tissue transgenic *Prunus* plantlets;
   d.) rooting said transgenic *Prunus* plantlets;
   e.) acclimating said rooted transgenic *Prunus* plantlets in a growth chamber;
   f.) planting said acclimated transgenic *Prunus* plantlets in a temperature controlled greenhouse;
   g.) selecting for a growing transgenic *Prunus* plant comprising said recombinant construct and exhibiting an early and continually flowering phenotype;
   h.) pollinating transgenic *Prunus* flowers on said growing transgenic *Prunus* plant with pollen from compatible *Prunus* cultivars;
   i.) selecting for a growing PtFT1 transgenic *Prunus* plant exhibiting an early and continually flowering phenotype and producing ripe fruits with fertile seeds comprising said recombinant construct;
   j.) germinating said seeds to produce a growing PtFT1 transgenic *Prunus* plant comprising said recombinant construct and exhibiting an early and continually flowering phenotype and bearing fully ripe *Prunus* fruit with fertile seeds;
   k.) crossing said PtFT1 transgenic *Prunus* plant exhibiting an early and continually flowering phenotype and bearing fully ripe *Prunus* fruit with fertile seeds of step (j.) to non-transformed *Prunus* plants exhibiting said new characteristics; and
   l.) selecting progeny *Prunus* plants that exhibit said new characteristics and do not carry the PtFTl transgene for use in conventional breeding to obtain improved non-transgenic cultivars and varieties of plants.

12. A method of producing *Prunus* fruit continuously in a protected structure such as a greenhouse comprising:
   a.) making a transgenic *Prunus* plant according to claim 6;
   b.) growing said *Prunus* plant to produce seeds comprising said recombinant construct;
   c.) growing said seeds to produce transgenic *Prunus* plants comprising said recombinant construct;
   d.) growing said transgenic *Prunus* plants in large numbers in a protected structure; and
   e.) allowing said *Prunus* plants to produce fruit continuously in said protected structure.

13. A method of providing continuous transgenic *Prunus* fruit production in protected structures such as a greenhouse comprising:

a.) making growing transgenic *Prunus* plants exhibiting an early and continually flowering phenotype and also producing ripe fruits with fertile seeds according to claim 11, steps a through j, wherein said growing transgenic *Prunus* plants are further characterized by a branched, upright growth pattern, a combination of branched, upright and branched, bushy growth pattern, or a combination of branched, bushy and branched, recumbent growth pattern when compared to a non-transgenic control plant;

b.) pollinating transgenic *Prunus* flowers on said growing transgenic *Prunus* plants with pollen from compatible *Prunus* cultivars to produce seeds comprising said construct and germinating the seeds to produce growing transgenic *Prunus* plants bearing fully ripe *Prunus* fruit with fertile seeds;

c.) selecting for a growing PtFT1 transgenic *Prunus* plant exhibiting bushy or recumbent growth characteristics and bearing ripe fruit with fertile seeds comprising said recombinant construct;

d.) germinating said seeds to produce PtFT1 transgenic *Prunus* plants comprising said recombinant construct and exhibiting an early and continually flowering phenotype and also bearing fully ripe *Prunus* fruit with fertile seeds;

e.) crossing said PtFT1 transgenic *Prunus* plants exhibiting an early and continually flowering phenotype and bushy or recumbent growth characteristics and producing ripe fruit with fertile seeds to non-transformed *Prunus* plants exhibiting said new characteristics;

f.) selecting for progeny *Prunus* plants that exhibit said new characteristics and carry the PtFT1 transgene for use in either conventional breeding to obtain improved varieties of plants or off-season fruit production; and g.) growing said plants in large numbers in an enclosed space.

14. A transgenic *Prunus* plant made by the method of claim 1, or progeny thereof, wherein said plant or progeny thereof comprises the PtFT1 recombinant construct and exhibits early flowering and a shortened juvenile period.

15. The transgenic *Prunus* plant of claim 14, or progeny thereof, wherein said plant or progeny thereof comprises the PtFTI construct and exhibits new flowering structures.

16. The transgenic *Prunus* plant of claim 14, or progeny thereof, wherein said plant or progeny thereof comprises the PtFT1 recombinant construct which result in PtFT1 lines which segregate both early flowering and non-flowering progeny wherein said non-flowering progeny do not carry any transgenes.

17. A transgenic *Prunus* plant made by the method of claim 6, or progeny thereof, wherein said plant or progeny thereof comprises the PtFT1 recombinant construct and exhibits early and continual flowering and production of fruit.

18. A transgenic *Prunus* plant made by the method of claim 6, or progeny thereof, wherein said plant or progeny thereof comprises the PtFT1 recombinant construct and exhibits a branched, upright growth pattern, a combination of branched, upright and branched, bushy growth pattern, or a combination of branched, bushy and branched, recumbent growth pattern when compared to a non-transgenic control plant.

19. The transgenic *Prunus* plant of claim 17, or progeny thereof, wherein said plant or progeny thereof comprises the PtFT1 recombinant construct and exhibits fruit production in a broader range of climates when compared to a non-transgenic control plant.

20. A plant cell, a plant part, or a plant tissue of the plant of any one of claims 14-19, wherein said plant cell, plant part or plant tissue comprise said recombinant construct.

21. A pollen grain from the transgenic plant according to any one of claims 14-19, wherein the pollen grain contains the PtFT1 recombinant construct.

22. A pistil from the transgenic plant according to any one of claims 14-19, wherein the pistil contains the PtFT1 recombinant construct.

23. A transgenic seed of the transgenic *Prunus* plant according to any one of claims 14-19, wherein the seed comprising the PtFT1 recombinant construct generates plants exhibiting early flowering and shortened juvenile period as compared to a wild type variety of the seed.

* * * * *

SEQUENCE LISTING

```
<160> NUMBER OF SEQ ID NOS: 12

<210> SEQ ID NO 1
<211> LENGTH: 525
<212> TYPE: DNA
<213> ORGANISM: Populus trichocarpa

<400> SEQUENCE: 1
atgtcaaggg acagagatcc tctgagcgtt ggccgtgtta taggggacgt gctggacccc      60
ttcacaaagt ctatctccct cagggtcact tacagctcca gagaggtcaa caatggttgc     120
gagctcaagc cctctcaggt tgccaaccag cctagggttg atattggcgg ggaagatcta     180
aggaccttct acactctggt tatggtggac cctgatgcac ccagcccaag tgaccccagc     240
ctaagagaat atttgcattg gttggtgact gatattccag caacaactgg ggcaagcttt     300
ggccatgaaa ctgtgtgcta tgagagcccg aggccgacaa tgggtattca tcggtttgtt     360
ttcgtcttgt ttcggcaact gggcaggcaa actgtgtatg cccctgggtg gcgccagaac     420
ttcaacacca gagactttgc tgaggtctac aatcttggat cgccagtggc tgctgtttat     480
ttcaactgcc agagggagag tggctctggt ggtaggaggc gataa                    525

<210> SEQ ID NO 2
<211> LENGTH: 174
<212> TYPE: PRT
<213> ORGANISM: Populus trichocarpa

<400> SEQUENCE: 2

Met Ser Arg Asp Arg Asp Pro Leu Ser Val Gly Arg Val Ile Gly Asp
  1               5                  10                  15

Val Leu Asp Pro Phe Thr Lys Ser Ile Ser Leu Arg Val Thr Tyr Ser
                 20                  25                  30

Ser Arg Glu Val Asn Asn Gly Cys Glu Leu Lys Pro Ser Gln Val Ala
             35                  40                  45

Asn Gln Pro Arg Val Asp Ile Gly Gly Glu Asp Leu Arg Thr Phe Tyr
         50                  55                  60

Thr Leu Val Met Val Asp Pro Asp Ala Pro Ser Pro Ser Asp Pro Ser
 65                  70                  75                  80

Leu Arg Glu Tyr Leu His Trp Leu Val Thr Asp Ile Pro Ala Thr Thr
                 85                  90                  95

Gly Ala Ser Phe Gly His Glu Thr Val Cys Tyr Glu Ser Pro Arg Pro
            100                 105                 110

Thr Met Gly Ile His Arg Phe Val Phe Val Leu Phe Arg Gln Leu Gly
        115                 120                 125

Arg Gln Thr Val Tyr Ala Pro Gly Trp Arg Gln Asn Phe Asn Thr Arg
    130                 135                 140

Asp Phe Ala Glu Val Tyr Asn Leu Gly Ser Pro Val Ala Ala Val Tyr
145                 150                 155                 160
```

Phe Asn Cys Gln Arg Glu Ser Gly Ser Gly Gly Arg Arg Arg
            165                 170

<210> SEQ ID NO 3
<211> LENGTH: 20
<212> TYPE: DNA
<213> ORGANISM: Unknown
<220> FEATURE:
<223> OTHER INFORMATION: Chemically Synthesized

<400> SEQUENCE: 3
cagaacttca acaccagaga                                               20

<210> SEQ ID NO 4
<211> LENGTH: 19
<212> TYPE: DNA
<213> ORGANISM: Unknown
<220> FEATURE:
<223> OTHER INFORMATION: Chemically Synthesized

<400> SEQUENCE: 4
tcctaccacc agagccact                                                19

<210> SEQ ID NO 5
<211> LENGTH: 25
<212> TYPE: DNA
<213> ORGANISM: Unknown
<220> FEATURE:
<223> OTHER INFORMATION: Chemically Synthesized

<400> SEQUENCE: 5
ttctacactc tggttatggt ggacc                                         25

<210> SEQ ID NO 6
<211> LENGTH: 22
<212> TYPE: DNA
<213> ORGANISM: Unknown
<220> FEATURE:
<223> OTHER INFORMATION: Chemically Synthesized

<400> SEQUENCE: 6
gttgccgaaa caagacgaaa ac                                            22

<210> SEQ ID NO 7
<211> LENGTH: 20
<212> TYPE: DNA
<213> ORGANISM: Unknown
<220> FEATURE:
<223> OTHER INFORMATION: Chemically Synthesized

<400> SEQUENCE: 7
gcagccaagc cttcatagcg                                               20

<210> SEQ ID NO 8
<211> LENGTH: 20
<212> TYPE: DNA
<213> ORGANISM: Unknown
<220> FEATURE:
<223> OTHER INFORMATION: Chemically Synthesized

<400> SEQUENCE: 8
gtgcgaatca acggttcctc                                               20

<210> SEQ ID NO 9
<211> LENGTH: 24
<212> TYPE: DNA

```
-continued

<213> ORGANISM: Unknown
<220> FEATURE:
<223> OTHER INFORMATION: Chemically Synthesized

<400> SEQUENCE: 9
gtgttcagac cacttccttc atcc                                              24

<210> SEQ ID NO 10
<211> LENGTH: 21
<212> TYPE: DNA
<213> ORGANISM: Unknown
<220> FEATURE:
<223> OTHER INFORMATION: Chemically Synthesized

<400> SEQUENCE: 10
ccatcttcaa ccttcggctt c                                                 21

<210> SEQ ID NO 11
<211> LENGTH: 23
<212> TYPE: DNA
<213> ORGANISM: Unknown
<220> FEATURE:
<223> OTHER INFORMATION: Chemically Synthesized

<400> SEQUENCE: 11
caaggcaact acaactcagg cag                                               23

<210> SEQ ID NO 12
<211> LENGTH: 24
<212> TYPE: DNA
<213> ORGANISM: Unknown
<220> FEATURE:
<223> OTHER INFORMATION: Chemically Synthesized

<400> SEQUENCE: 12
aggcatccca tacataacac caag                                              24
```